US007914513B2

(12) United States Patent
Voorhees, Jr.

(10) Patent No.: US 7,914,513 B2
(45) Date of Patent: Mar. 29, 2011

(54) METHOD OF USING A MULTI-LUMEN CATHETER ASSEMBLY

(75) Inventor: Earl W. Voorhees, Jr., Warrington, PA (US)

(73) Assignee: Medical Components, Inc., Harleysville, PA (US)

( * ) Notice: Subject to any disclaimer, the term of this patent is extended or adjusted under 35 U.S.C. 154(b) by 1354 days.

(21) Appl. No.: 11/190,529

(22) Filed: Jul. 27, 2005

(65) Prior Publication Data

US 2005/0261665 A1    Nov. 24, 2005

Related U.S. Application Data

(62) Division of application No. 10/366,260, filed on Feb. 13, 2003, now Pat. No. 6,969,381.

(60) Provisional application No. 60/434,304, filed on Dec. 18, 2002.

(51) Int. Cl.
*A61M 31/00* (2006.01)
*A61M 3/00* (2006.01)

(52) U.S. Cl. ............................ 604/508; 604/500; 604/43

(58) Field of Classification Search .................. 604/508, 604/500, 43
See application file for complete search history.

(56) References Cited

U.S. PATENT DOCUMENTS

| | | | |
|---|---|---|---|
| 2,369,860 A | 2/1945 | Schroeder | |
| 4,405,163 A | 9/1983 | Voges et al. | |
| 4,405,312 A * | 9/1983 | Gross et al. | 604/29 |
| 4,508,367 A | 4/1985 | Oreopoulos et al. | |
| 4,631,056 A * | 12/1986 | Dye | 604/111 |
| 4,895,561 A * | 1/1990 | Mahurkar | 604/43 |
| 4,950,255 A | 8/1990 | Brown et al. | |
| 5,059,170 A | 10/1991 | Cameron | |
| 5,120,324 A | 6/1992 | Sancoff | |
| 5,171,216 A | 12/1992 | Dasse et al. | |
| 5,248,306 A | 9/1993 | Clark et al. | |
| 5,376,073 A | 12/1994 | Graves et al. | |
| 5,533,996 A | 7/1996 | Murphey et al. | |
| 5,575,767 A | 11/1996 | Stevens | |
| 5,743,873 A | 4/1998 | Cai et al. | |
| 5,755,695 A | 5/1998 | Erickson et al. | |
| 5,954,708 A | 9/1999 | Lopez et al. | |
| 5,976,115 A | 11/1999 | Parris et al. | |
| 5,989,240 A | 11/1999 | Strowe | |
| 5,993,437 A | 11/1999 | Raoz | |
| 6,083,207 A * | 7/2000 | Heck | 604/256 |
| 6,099,519 A * | 8/2000 | Olsen et al. | 604/534 |
| 6,155,611 A | 12/2000 | Lemire | |
| 6,190,349 B1 * | 2/2001 | Ash et al. | 604/43 |
| 6,248,092 B1 | 6/2001 | Miraki et al. | |
| 6,254,589 B1 | 7/2001 | Raoz | |
| 6,423,053 B1 | 7/2002 | Lee | |

(Continued)

*Primary Examiner* — Nicholas D Lucchesi
*Assistant Examiner* — Ian K Holloway
(74) *Attorney, Agent, or Firm* — Anton P. Ness, Esq.; Fox Rothschild LLP

(57) ABSTRACT

A multi-lumen catheter assembly with a two-piece hub is disclosed. The catheter includes a distal portion having a plurality of catheter lumens, wherein each of the plurality of catheter lumens includes a distal tip and a proximal lumen portion. The distal portion further includes a distal hub portion slidably disposed over the proximal lumen portion, wherein the distal hub portion includes a pivoting locking member. The catheter assembly further includes a proximal portion having a plurality of catheter extensions, wherein each of the plurality of catheter extensions fluidly communicates with at least one of the plurality of catheter lumens. The proximal portion also includes a proximal hub portion having a locking receiver, wherein the pivoting locking member is releasably engaged with the locking receiver.

11 Claims, 5 Drawing Sheets

U.S. PATENT DOCUMENTS

| | | | |
|---|---|---|---|
| 6,508,807 B1 * | 1/2003 | Peters | 604/533 |
| 7,261,708 B2 * | 8/2007 | Raulerson | 604/523 |
| 7,381,204 B2 * | 6/2008 | Wilson et al. | 604/500 |
| 7,458,955 B2 * | 12/2008 | Owens et al. | 604/117 |
| 2002/0099326 A1 * | 7/2002 | Wilson et al. | 604/43 |
| 2003/0088213 A1 * | 5/2003 | Schweikert et al. | 604/177 |
| 2004/0034324 A1 * | 2/2004 | Seese et al. | 604/246 |
| 2004/0059314 A1 * | 3/2004 | Schon et al. | 604/544 |
| 2004/0092863 A1 * | 5/2004 | Raulerson et al. | 604/43 |
| 2004/0097903 A1 * | 5/2004 | Raulerson | 604/523 |
| 2004/0186444 A1 * | 9/2004 | Daly et al. | 604/247 |

\* cited by examiner

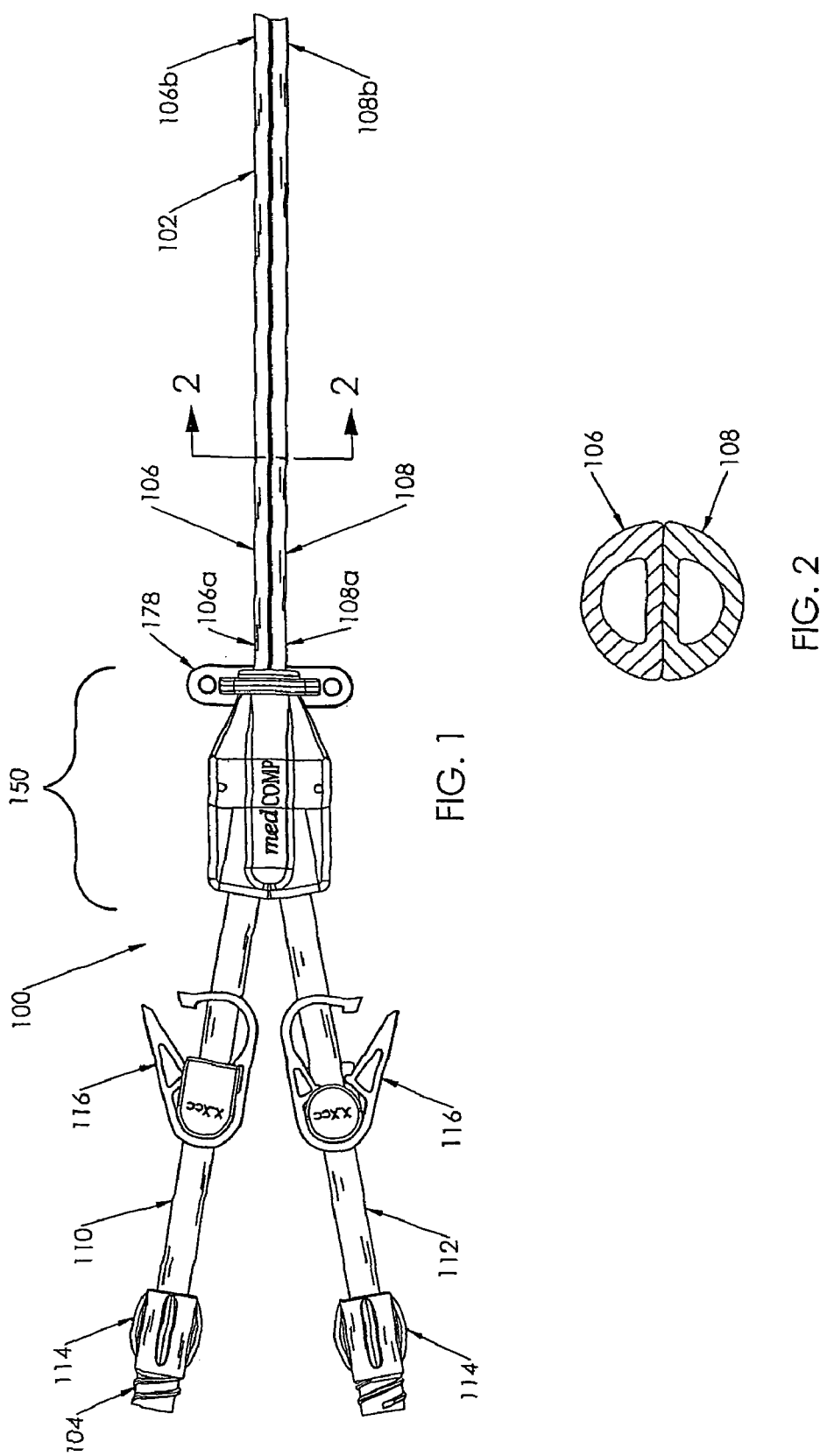

METHOD OF USING A MULTI-LUMEN CATHETER ASSEMBLY

CROSS REFERENCE TO RELATED APPLICATION

This application is a divisional of copending application Ser. No. 10/336,260, filed Feb. 13, 2003, entitled Multi-Lumen Catheter with Detachable Locking Hub" which claims priority from U.S. Provisional Patent Application Ser. No. 60/434,304 filed on Dec. 18, 2002, the entire disclosures of which are incorporated herein by reference.

FIELD OF THE INVENTION

The present invention relates to a multi-lumen catheter having a hub with multiple pieces that lock together.

BACKGROUND OF THE INVENTION

Catheters for the introduction or removal of fluids may be located in various venous locations and cavities throughout the body for introduction of fluids to the body or removal of fluids from the body. Such catheterization may be performed by using a single catheter having multiple lumens. A typical example of a multiple lumen catheter is a dual lumen catheter assembly in which one lumen introduces fluid and the other lumen removes fluid. An example of such a dual lumen catheter assembly is the ASH SPLIT-CATH® catheter.

Generally, to insert any catheter into a blood vessel, the vessel is identified by aspiration with a long hollow needle in accordance with the well known Seldinger technique. When blood enters a syringe attached to the needle, indicating that the vessel has been found, a thin guidewire is then introduced, typically through a syringe needle or other introducer device into the interior of the vessel. The introducer device is then removed, leaving the guidewire within the vessel. The guidewire projects beyond the surface of the skin. At this point, several options are available to a physician for catheter placement. The simplest is to pass a catheter into the vessel directly over the guidewire. The guidewire is then removed, leaving the catheter in position within the vessel. However, this technique is only possible in cases where the catheter (for example, a small diameter dual lumen catheter) is of a relatively small diameter, made of a stiff material, and not significantly larger than the guidewire. If the catheter to be inserted is significantly larger than the guidewire, a dilator device is passed over the guidewire to enlarge the opening in the vessel. The catheter is then passed over the guidewire into the vessel, and the guidewire and dilator are then removed, leaving the catheter in position within the vessel.

For chronic catheterization, in which the catheter is intended to remain inside the patient for an extended period of time, such as for weeks or even months, it is typically desired to subcutaneously tunnel the catheter into the patient using various tunneling techniques. The catheter is typically tunneled into the patient prior to inserting the catheter into the patient's vein. However, there may be times when it is more advantageous, due to such things as the patient or the implanting surgeon's skill, to perform the tunneling after the catheter is implanted in the patient. For some catheters, though, such as multiple lumen catheters with a hub and with bonded luers on the proximal ends of the catheters, it is impractical to perform the tunneling after the catheter is installed in the patient. It would be beneficial to provide a catheter assembly that provides a surgeon with alternative installation procedures for instaling the catheter that better suit either the patient's needs or the surgeon's skills.

Further, for chronically installed catheters, portions of the catheter external to the patient occasionally fail, such as for instance, by leaking and/or by the introduction of foreign particles such as dirt, bacteria, and the like into the catheter. Such failures include worn or broken clamps or broken luers. In order to correct these problems, it is presently necessary to remove the entire catheter from the patient, causing additional trauma and risking additional medical problems to the patient. It would be beneficial to provide a catheter in which the proximal portion of the catheter may be removed and replaced without disturbing the distal portion of the catheter inside the patient.

BRIEF SUMMARY OF THE INVENTION

Briefly, the present invention provides a detachable hub for a catheter, comprising a first portion having a first distal end, a first proximal end, and a longitudinal channel extending therethrough between the first distal end and the first proximal end, wherein the first proximal end includes a pivoting locking member. The hub further comprises a second portion having a second distal end, and a second proximal end, wherein the second distal end includes a locking receiver, and wherein the longitudinal channel of the first portion of the hub is sized to allow the first proximal end to be disposed over the second distal end such that the pivoting locking member is engageable with the locking receiver.

Additionally, the present invention provides a multi-lumen catheter assembly, comprising a distal portion having a plurality of catheter lumens, wherein each of the plurality of catheter lumens includes a distal tip and a proximal lumen portion. The distal portion further comprises a distal hub portion slidably disposed over the proximal lumen portion, wherein the distal hub portion includes a pivoting locking member. In addition to the distal hub portion, the hub of the catheter assembly also comprises a proximal hub portion having a plurality of catheter extensions, wherein each of the plurality of catheter extensions fluidly communicates with at least one of the plurality of catheter lumens. The proximal hub portion has a locking receiver, wherein the pivoting locking member of the distal hub portion of the hub is releasably engaged with the locking receiver of the proximal hub portion.

The present invention also provides a method of inserting a multi-lumen catheter assembly into a patient. The method comprises inserting a distal end of each of a plurality of catheter lumens into a patient's blood vessel; connecting a proximal end of each of the plurality of catheter lumens to a tunneling device; forming a subcutaneous tunnel with the tunneling device; pulling the proximal ends of the plurality of catheter lumens through the subcutaneous tunnel; disconnecting the tunneling device from the proximal ends of the plurality of catheter lumens; sliding a first portion of a catheter hub over the proximal ends of the plurality of catheter lumens, wherein the first portion of the catheter hub comprises a pivoting locking member; connecting a second portion of the catheter hub to each of the plurality of catheter lumens, wherein the second portion of the catheter hub comprises a locking receiver; and engaging the pivoting locking member with the locking receiver.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a side view of a catheter assembly according to a preferred embodiment of the present invention.

FIG. 2 is a sectional view of a pair of catheter lumens taken along line 2-2 of FIG. 1.

DETAILED DESCRIPTION OF THE INVENTION

Figure 3:
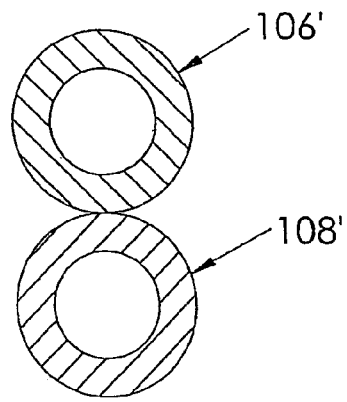
FIG. 3 is a sectional view of an alternative embodiment of a pair of catheter lumens.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of the catheter in the catheter assembly according to the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Referring to FIG. 1, a catheter assembly 100 incorporating a snap hub 150 according to a first preferred embodiment of the present invention is shown. The catheter assembly 100 includes a distal end 102 and a proximal end 104. The distal end 102 includes a plurality of catheter lumens 106, 108. While two catheter lumens 106, 108 are shown, those skilled in the art will recognize that a catheter assembly utilizing more than two catheter lumens 106, 108 is within the scope of the present invention. As seen in FIG. 2, the catheter lumens 106, 108 preferably have generally "D-shaped" cross-sections along at least a majority of the length of each catheter lumen 106, 108, with the generally flat portion of the D-shape of each catheter lumen 106, 108 in juxtaposed relation with each other. The generally flat portion of the D-shape of each catheter lumen 106, 108 is preloaded to bow outward slightly to improve sealing around each catheter lumen 106, 108, as is described in more detail herein.

Referring back to FIG. 1, proximal ends 106a, 108a of the catheter lumens 106, 108 are preferably joined together, with distal ends 106b, 108b of the catheter lumens 106, 108 preferably splittable from each other, such as the catheter lumens of the ASH SPLIT-CATH® catheter, manufactured and sold by Medical Components, Inc., of Harleysville, Pa. Alternatively, the distal ends 106b, 108b of the catheter lumens 106, 108 may be fixedly split from each other. In a second preferred embodiment of catheter lumens, as shown in FIG. 3, the catheter lumens 106', 108' may have generally circular cross-sections along at least a majority of the length of each catheter lumen. The catheter lumens 106', 108' may be fixedly or splittably joined together along at least a portion of their lengths, or the catheter lumens 106', 108' may be separate and distinct from each other.

As seen in FIG. 1, catheter lumen 106 is shorter than catheter lumen 108. With this configuration, it is preferred that the catheter lumen 106 be used to draw fluid, such as blood, from the patient, and that the catheter lumen 108 be used to return the fluid to the patient after treatment, such as hemodialysis.

The proximal end 104 of the catheter assembly 100 includes a pair of extension tubes 110, 112 that fluidly communicate with the catheter lumens 106, 108 through the hub 150, as is described in more detail herein. Each extension tube 110, 112 includes a connection device 114, such as a luer lock, disposed at the most proximal end of the extension tubes 110, 112. An extension clamp 116 is disposed over each extension tube 110, 112, between each connection device 114 and the hub 150. Preferably, the extension clamp 116 is a Roberts clamp, or some other clamp known to those skilled in the art.

Figure 4:
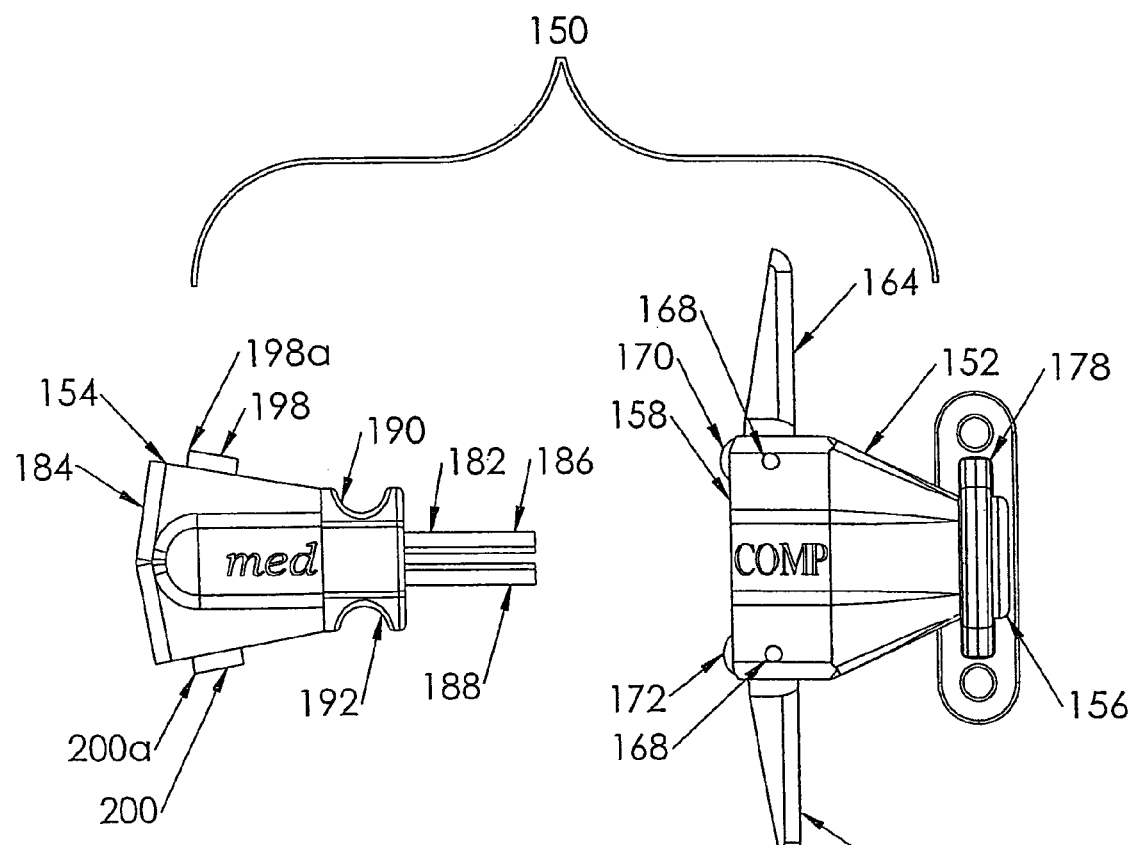
FIG. 4 is an exploded view of a catheter hub according to a preferred embodiment of the present invention.
Figure 5:
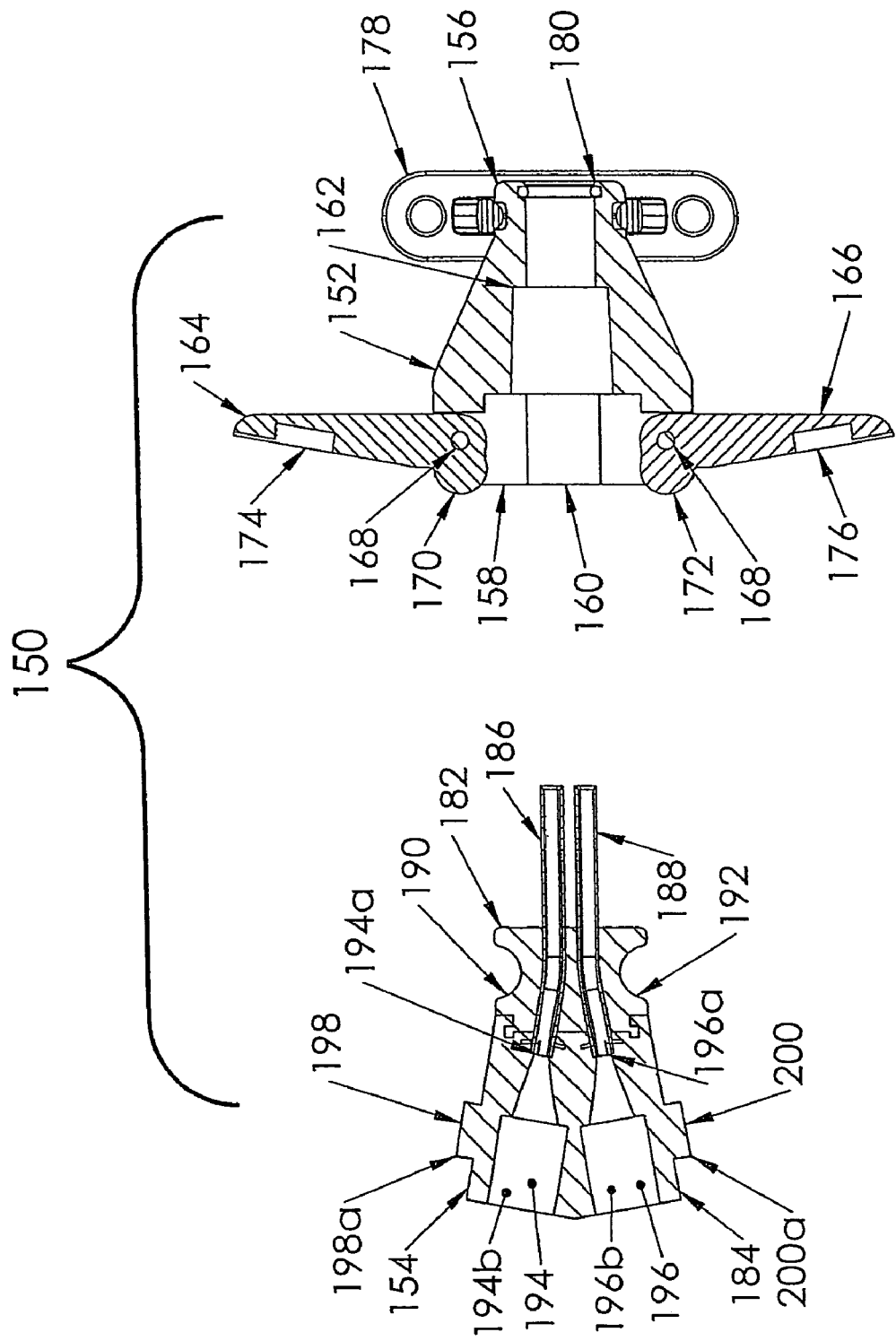
FIG. 5 is a sectional view of the catheter hub taken along line 5-5 of FIG. 4.

Referring now to FIGS. 4 and 5, the hub 150 is comprised of a distal portion 152 and a separable proximal portion 154. The distal portion 152 includes a distal end 156 and a proximal end 158. A longitudinal channel 160 extends through the distal portion 152 between the distal end 156 and the proximal end 158. As is seen in FIG. 5, the channel 160 is wider at the proximal end 158 than at the distal end 156. The channel 160 includes a shoulder 162 that narrows the channel 160 between the proximal end 158 and the distal end 156. The channel 160 is sized to allow the distal portion 152 of the hub 150 to be disposed over the proximal ends of the catheter lumens 106, 108.

The distal portion 152 of the hub 150 further includes first and second pivoting locking members 164, 166, respectively, which serve to lock the distal portion 152 to the proximal portion 154. Each locking member 164, 166 includes a pivot axle 168, about which each locking member 164, 166 rotates. Proximate to each respective pivot axle 168, the locking members 164, 166 each include a cam 170, 172, respectively, which engage the proximal portion 154 when the locking members 164, 166 are moved to a locking position. Each locking member 164, 166 further includes a recess 174, 176, respectively, that engages a proximal end of the proximal portion 154 when the locking members 164, 166 engage the proximal portion 154.

The distal end 156 of the distal portion 152 further includes a suture wing 178 disposed thereon. Preferably, the suture wing 178 is rotatable about the longitudinal channel 160, although those skilled in the art will recognize that the suture wing 178 may be fixed to the distal portion 152, instead. Preferably, the distal portion 152 and the suture wing 178 are each constructed from Pellethane, although those skilled in the art will recognize that the distal portion 152 and the suture wing 178 may be constructed from other suitable materials. An o-ring 180 may be disposed within the channel 160 proximate to the distal end 156 of the distal portion 152. The o-ring 180 provides a generally leak-proof seal between the catheter lumens 106, 108 and the distal portion 152 of the hub 150 when the distal portion 152 is disposed over the catheter lumens 106, 108. However, those skilled in the art will recognize that the o-ring 180 may be omitted entirely.

The proximal portion 154 of the hub 150 includes a distal end 182 and a proximal end 184. The distal end 182 of the proximal portion 154 includes first and second hub cannulae 186, 188, which are sized and shaped to enable the proximal ends 106a, 106b of the catheter lumens 106, 108 to be fittingly disposed over a respective hub cannula 186, 188, respectively.

The distal end 182 of the proximal portion 154 of the hub 150 also includes first and second locking receivers 190, 192, respectively. The locking receivers 190, 192 are each preferably generally saddle-shaped such that, when the proximal end 158 of the distal portion 152 is disposed over the distal end 182 of the proximal portion 154, the cams 170, 172 engage their respective locking receiver 190, 192.

The proximal end 184 of the proximal portion 154 of the hub 150 includes first and second channels 194, 196 that each have a distal end 194a, 196a fluidly communicating with a respective hub cannula 186, 188. A proximal end 194b, 196b of each channel 194, 196 is sized to accept the extension tubes 110, 112, respectively so that the proximal ends 194b, 196b each fluidly communicate with a respective extension tube 110, 112. The channel 194 fluidly communicates with the hub cannula 186 and the channel 196 fluidly communicates with the hub cannula 188 so that channels are formed through the length of the second portion 154.

Further, the proximal end 184 of the proximal portion 154 includes projections 198, 200 extending therefrom, generally away from the channels 194, 196, respectively. The projections 198, 200 are sized and disposed such that, when the proximal end 158 of the distal portion 152 is disposed over the distal end 182 of the proximal portion 154, the projections 198, 200 are received within the recesses 174, 176, respectively. The projections 198, 200 are preferably generally orthogonally shaped; however, the proximal edge 198a, 200a of each projection 198, 200 is preferably slightly chamfered to allow the respective recess 174, 176 to fit over the proximal edge 198a, 200a.

The proximal end 158 of the distal portion 152, as well as the channel 160, are sized to allow the proximal end 158 of the distal portion 152 to be disposed over the distal end 182 of the distal portion 154 such that each cam 170, 172 is engageable with a respective locking receiver 190, 192.

Preferably, the proximal end 184 of the proximal portion 154 is constructed from Pellethane and the distal end 182 of the proximal portion 154 is constructed from Tecoplast, although those skilled in the art will recognize that both the proximal end 184 and the distal end 182 may be constructed from other, suitable materials. Further, the hub cannulae 186, 188 are preferably constructed from 304 stainless steel, although those skilled in the art will recognize that other suitable materials may be used.

While it is preferred that the distal portion 152 of the hub 150 includes the pivoting locking members 164, 166 and that the proximal portion 154 of the hub 150 includes the first and second locking receivers 190, 192, those skilled in the art will recognize that the distal portion 152 of the hub 150 may incorporate the locking receivers 190, 192 and that the proximal portion 154 of the hub 150 may incorporate the pivoting locking members 164, 166 without departing from the scope of the present invention.

Figure 6:
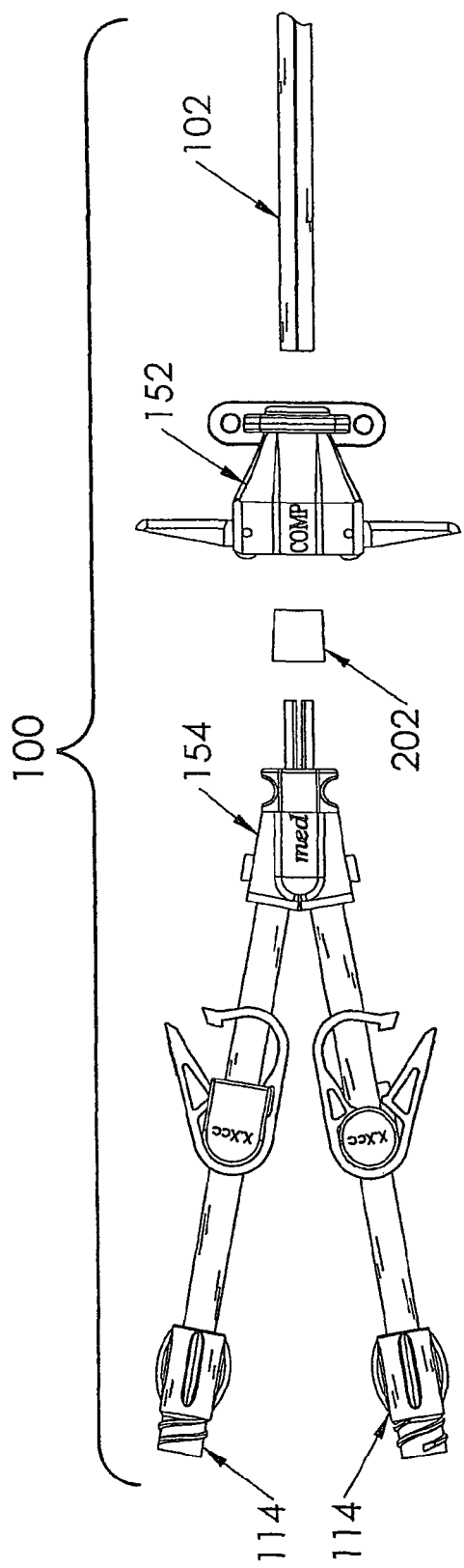
FIG. 6 is a side exploded view showing the elements of the catheter assembly.
Figure 7:
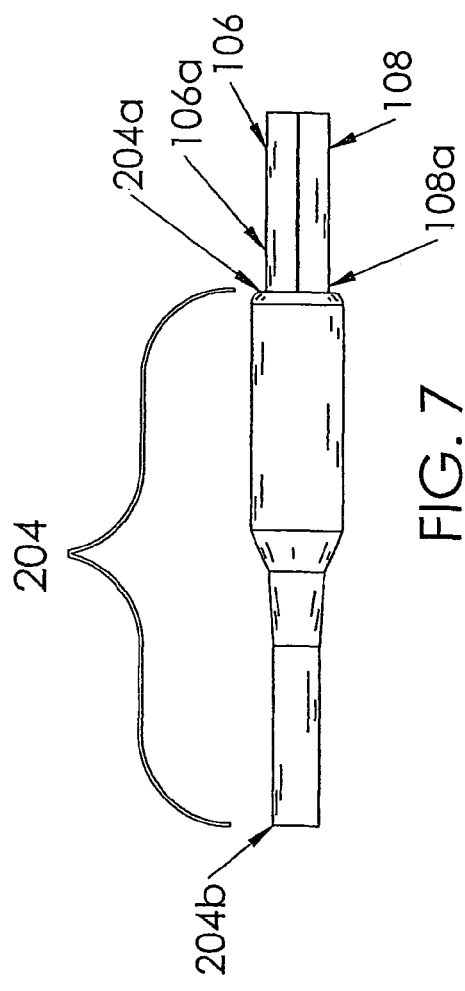
FIG. 7 is a perspective view of a catheter tunneler connected to proximal ends of the catheter lumens of FIG. 2.

The catheter assembly 100 is preferably provided for use in kit form, with the catheter 102, the distal portion 152 of the hub 150, and the proximal portion 154 of the hub 150, as well as a compression ring 202, all separate, as shown in FIG. 6. The catheter assembly 100 is inserted into a patient by inserting the distal end of the catheter 102 into the patient's blood vessel according to known techniques. Referring now to FIG. 7, a distal end 204a of a dual lumen catheter tunneler 204 is connected to the proximal ends 106a, 108a of each catheter lumen 106, 108. An embodiment of a preferred dual lumen catheter tunneler 204 is disclosed in U.S. Provisional Patent Application Ser. No. 60/434,303, filed on Dec. 18, 2002, which is owned by the Assignee of the present invention and which is incorporated herein by reference in its entirety. A proximal end 204b of the tunneler 204 is inserted under the patient's skin forming a subcutaneous tunnel. The proximal ends 106a, 108a of the catheters lumens 106, 108 are pulled through the subcutaneous tunnel, and the tunneler 204 is disconnected from the catheter lumens 106, 108.

Referring back to FIGS. 5 and 6, the proximal ends 106a, 108a of the catheter lumens 106, 108 are inserted into the channel 160 from the distal end 156 of the distal portion 152 of the hub 150 and the distal portion 152 of the hub 150 is slid over the proximal ends 106a, 108a of the catheter lumens 106, 108. Optionally, but preferably, the compression ring 202 is next slid over the proximal ends 106a, 108a of the catheter lumens 106, 108. The hub cannulae 186, 188, whose distal end portions are disposed in the proximal portion 154 of the hub 150, are next slid into the proximal ends 106a, 108a of the catheter lumens 106, 108, respectively, so that the proximal portion 154 of the hub 150 and the catheter lumens 106, 108 are in fluid communication with each other. The slight outward bow of the generally flat portion of the catheter lumens 106, 108 improves sealing between the lumens 106, 108 and the hub cannulae 186, 188 when the compression ring 202 is compressed. Further, the hub cannulae 186, 188 generally bias toward each other to again improve the sealing. The compression ring 202 is slid proximally over the catheter lumens 106, 108 so that the compression ring 202 is disposed over the hub cannulae 186, 188. The compression ring 202 serves to seal the catheter lumens 106, 108 on the hub cannulae 186, 188.

Next, the distal portion 152 of the hub 150 is advanced toward the proximal portion 154 of the hub 150. When the distal portion 152 and the proximal portion 154 are engaged with each other, the locking members 164, 166 are pivoted about their pivot axles 168 so that the cam 170 is disposed in the saddle 190 and so that the cam 172 is disposed in the saddle 192. The eccentricity of the cams 170, 172 exerts a camming action between the cams 170, 172 and their respective saddles 190, 192, locking the distal portion 152 and the proximal portion 154 of the hub 150 to each other. Additionally, the projections 198, 200 are disposed within their respective recesses 174, 176 on the locking members 164, 166, respectively, further securing the distal portion 152 to the proximal portion 154.

The catheter assembly 100 is secured to the patient by suturing the suture wing 178 to the patient's skin. The catheter 100 is now fully assembled and the luer locks 114 are ready to be connected to an outside machine, such as a dialysis machine (not shown).

If, after the distal portion 102 of the catheter assembly 100 has been inserted into the patient, and a portion of the catheter assembly 100, such as, for example, a luer lock 114 which may have broken, is required to be replaced, the hub 150 may be disassembled, and the proximal end 104 of the catheter assembly 100 may be replaced, without having to remove the catheter lumens 106, 108 from the patient.

Figure 8:
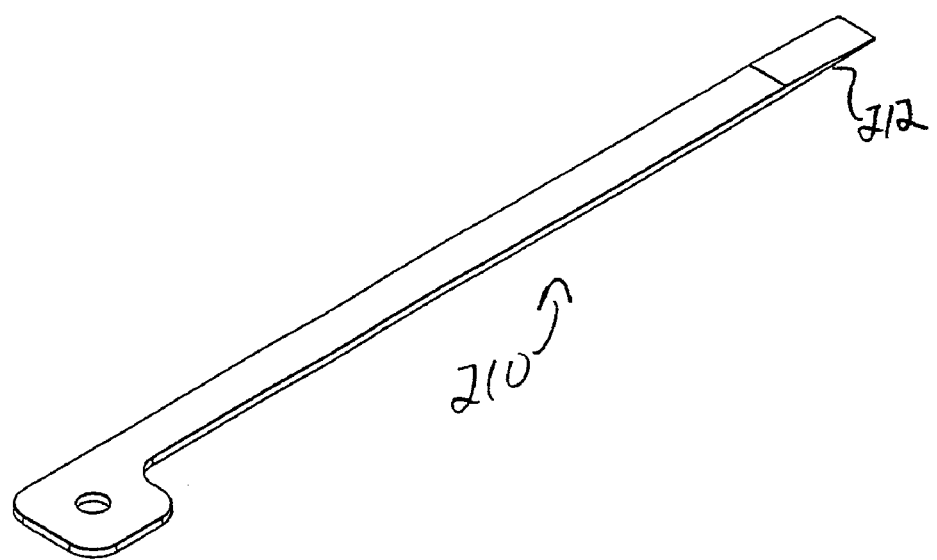
FIG. 8 is a perspective view of a hub disassembly tool.

A hub disassembly tool 210, shown in perspective in FIG. 8, may be used to unlock the locking members 174, 176 from the proximal end 154 of the hub 150. A blade end 212 of the tool 210 is serially inserted between the proximal ends of each locking member 174, 176 and the proximal end 154 of the hub 150. The tool 210 operates as a lever to assist a medical technician in unlocking the locking members 174, 176 from the proximal end 154 of the hub 150.

After the locking members 174, 176 are unlocked from the proximal end 154 of the hub 150 and rotated to displace the cams 170, 172 from their respective saddles 190, 192, the distal hub portion 152 is separated from the proximal hub portion 154, and the compression ring 202 is slid distally along the catheter lumens 106, 108. The hub cannulae 186, 188 are now removed from their respective catheter lumens 106, 108. Replacement pieces are now utilized in the place of broken pieces or pieces that otherwise may need to be replaced, and the catheter is reassembled as described above.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of inserting a multi-lumen catheter assembly into a patient comprising:
   providing a plurality of catheter lumens and initially separate first and second hub portions complementary to each other;
   inserting a distal end of each of a plurality of catheter lumens into a patient's blood vessel;
   connecting a proximal end of each of the plurality of catheter lumens to a tunneling device;
   forming a subcutaneous tunnel with the tunneling device;
   pulling the proximal ends of the plurality of catheter lumens through the subcutaneous tunnel;
   disconnecting the tunneling device from the proximal ends of the plurality of catheter lumens;
   sliding the first portion of a catheter hub over the proximal ends of the plurality of catheter lumens, wherein the first portion of the catheter hub comprises at least one pivoting locking member;
   connecting the second portion of the catheter hub to each of the plurality of catheter lumens, wherein the second portion of the catheter hub comprises at least one locking receiver; and
   pivotally moving each at least one pivoting locking member about a respective transverse axis and engaging a respective at least one pivoting locking member with a respective at least one locking receiver, whereby the second hub portion may be previously affixable to extension tube assemblies to define a proximal assembly manipulatable as a unit to be affixed to the first hub portion to complete the catheter implantation procedure with minimal steps to be performed by the practitioner at the patient bedside.

2. The method according to claim 1, further comprising, prior to connecting the second portion of the catheter hub to each of the plurality of lumens, inserting a compression ring over each of the plurality of lumens proximal to the first portion of the catheter hub.

3. The method according to claim 1, wherein the at least one pivoting locking member comprises a first locking member and a second locking member, and the at least one locking receiver comprises a first locking receiver and a second locking receiver, and wherein engaging the at least one pivoting locking member with a respective at least one locking receiver comprises engaging the first pivoting locking member with the first locking receiver and engaging the second pivoting locking member with the second locking receiver.

4. The method according to claim 1, further comprising the step of connecting additional parts, including a plurality of extension tubes, directly or indirectly to the second portion of the catheter hub.

5. The method according to claim 1, wherein the catheter assembly is comprised of parts, wherein the method further comprises the steps of:
   pivotally disengaging the at least one pivoting locking member from a respective at least one locking receiver;
   disconnecting the second portion of the catheter hub from each of the plurality of catheter lumens;
   replacing a part of the catheter assembly that has broken with a replacement part;
   reconnecting the portion of the catheter hub to each of the plurality of catheter lumens; and
   reengaging the at least one pivoting locking member with the respective at least one locking receiver,
   whereby a part of the catheter assembly may be removed and replaced without disturbing the catheter lumens inside the patient.

6. A method of inserting a multi-lumen catheter assembly into a patient comprising:
   providing a plurality of catheter lumens and initially separate first and second hub portions complementary to each other;
   inserting a distal end of each of a plurality of catheter lumens into a patient's blood vessel;
   connecting a proximal end of each of the plurality of catheter lumens to a tunneling device;
   forming a subcutaneous tunnel with the tunneling device;
   pulling the proximal ends of the plurality of catheter lumens through the subcutaneous tunnel;
   disconnecting the tunneling device from the proximal ends of the plurality of catheter lumens;
   sliding the first portion of a catheter hub over the proximal ends of the plurality of catheter lumens, wherein the first portion of the catheter hub comprises one of an at least one pivoting locking member or a complementary at least one locking receiver;
   connecting the second portion of the catheter hub to each of the plurality of catheter lumens, wherein the second portion of the catheter hub comprises the other of an at least one pivoting locking member or a complementary at least one locking receiver; and
   pivotally moving the at least one pivoting member about a respective transverse axis and engaging the at least one pivoting locking member with the respective at least one locking receiver whereby the second hub portion may be previously affixable to extension tube assemblies to define a proximal assembly manipulatable as a unit to be affixed to the first hub portion to complete the catheter implantation procedure with minimal steps to be performed by the practitioner at the patient bedside.

7. A method of inserting a multi-lumen catheter assembly into a patient comprising:
   inserting a distal end of each of a plurality of catheter lumens into a patient's blood vessel;
   connecting a proximal end of each of the plurality of catheter lumens to a tunneling device;
   forming a subcutaneous tunnel with the tunneling device;
   pulling the proximal ends of the plurality of catheter lumens through the subcutaneous tunnel;
   disconnecting the tunneling device from the proximal ends of the plurality of catheter lumens;
   sliding a first portion of a catheter hub over the proximal ends of the plurality of catheter lumens, wherein the first portion of the catheter hub comprises a first distal end, a first proximal end, and a longitudinal channel extending therethrough, wherein the first proximal end includes at least one pivoting locking member;
   connecting a second portion of the catheter hub to each of the plurality of catheter lumens, wherein the second portion of the catheter hub comprises a second distal end, a second proximal end, wherein the second distal end includes a respective at least one locking receiver; and
   pivotally moving the at least one pivoting member about a respective transverse axis and engaging the at least one pivoting locking member with the respective at least one locking receiver such that the first proximal end of the first portion is disposed over the second distal end of the second portion.

8. The method according to claim 7, further comprising, prior to connecting the second portion of the catheter hub to each of the plurality of lumens, inserting a compression ring over each of the plurality of lumens proximal to the first portion of the catheter hub.

9. The method according to claim 7, wherein the at least one pivoting locking member comprises a first locking member and a second locking member, and the at least one locking receiver comprises a first locking receiver and a second locking receiver, and wherein engaging the at least one pivoting locking member with a respective at least one locking receiver comprises engaging the first pivoting locking member with the first locking receiver and engaging the second pivoting locking member with the second locking receiver.

10. The method according to claim 7, further comprising the step of connecting additional parts, including a plurality of extension tubes, directly or indirectly to the second portion of the catheter hub.

11. The method according to claim 7, wherein the catheter assembly is comprised of parts, wherein the method further comprises the steps of:
   pivotally disengaging each at least one pivoting locking member from the respective at least one locking receiver;
   disconnecting the second portion of the catheter hub from each of the plurality of catheter lumens;
   replacing a part of the catheter assembly that has broken with a replacement part;
   reconnecting the portion of the catheter hub to each of the plurality of catheter lumens; and
   reengaging each at least one pivoting locking member with the respective at least one locking receiver,
   whereby a part of the catheter assembly may be removed and replaced without disturbing the catheter lumens inside the patient.

* * * * *